(12) United States Patent
Pyles et al.

(10) Patent No.: US 8,880,191 B2
(45) Date of Patent: Nov. 4, 2014

(54) METHOD OF IMPLANTING A SPINAL CORD STIMULATOR LEAD HAVING MULTIPLE OBSTRUCTION-CLEARING FEATURES

(71) Applicants: Stephen T. Pyles, Ocala, FL (US); Daniel A. Graubert, Etna, NH (US)

(72) Inventors: Stephen T. Pyles, Ocala, FL (US); Daniel A. Graubert, Etna, NH (US)

(73) Assignee: Stephen Pyles, Ocala, FL (US)

( * ) Notice: Subject to any disclaimer, the term of this patent is extended or adjusted under 35 U.S.C. 154(b) by 0 days.

(21) Appl. No.: 14/281,350

(22) Filed: May 19, 2014

(65) Prior Publication Data

US 2014/0288575 A1    Sep. 25, 2014

Related U.S. Application Data

(60) Continuation-in-part of application No. 13/270,501, filed on Oct. 11, 2011, now abandoned, and a division of application No. 11/421,098, filed on May 31, 2006, now abandoned, which is a continuation-in-part of application No. 11/217,061, filed on Aug. 31, 2005, now abandoned.

(60) Provisional application No. 60/606,172, filed on Aug. 31, 2004.

(51) Int. Cl.
*A61N 1/00* (2006.01)
*A61B 17/3203* (2006.01)
*A61M 29/02* (2006.01)
*A61N 1/05* (2006.01)

(52) U.S. Cl.
CPC .......... *A61N 1/0551* (2013.01); *A61B 17/3203* (2013.01); *A61M 29/02* (2013.01)
USPC ..................................... 607/117; 604/102.02

(58) Field of Classification Search
None
See application file for complete search history.

(56) References Cited

U.S. PATENT DOCUMENTS

| | | | |
|---|---|---|---|
| 3,435,826 A | * | 4/1969 | Fogarty |
| 3,448,739 A | * | 6/1969 | Stark et al. |
| 4,519,403 A | * | 5/1985 | Dickhudt |
| 4,526,175 A | * | 7/1985 | Chin et al. |
| 4,538,624 A | * | 9/1985 | Tarjan |
| 4,762,130 A | * | 8/1988 | Fogarty et al. |

(Continued)

OTHER PUBLICATIONS

Advanced Neuromodulation Systems, Inc.; ANS Percutaneous Leads; Jan. 6, 2006, 2 pgs.; www.ans-medical.com/medicalprofessional/physician/anspercutaneousleads.cfm.*

(Continued)

*Primary Examiner* — Mark W Bockelman
(74) *Attorney, Agent, or Firm* — Gardner Groff Greenwald & Villanueva, P.C.

(57) ABSTRACT

A method of implanting a spinal cord stimulator lead in the epidural space of a human or animal subject. The method includes discharging a first pressurized fluid through a first lumen in the stimulator lead directly onto a tissue obstruction to form a partial/pilot or full/final opening in the tissue obstruction. If a full opening was not formed sufficient for passage of the stimulator lead, the method further includes inserting a distal-end portion of the stimulator lead into the partial opening and then delivering a second pressurized fluid through a second lumen in the spinal cord stimulator lead and into a balloon for expanding a distensible balloon to clear the tissue obstruction sufficient for passage of the stimulator lead. The method further comprising advancing the stimulator lead past the cleared tissue obstruction and into place for use to deliver therapeutic energy to spinal tissue adjacent the contacts.

20 Claims, 9 Drawing Sheets

(56) References Cited

U.S. PATENT DOCUMENTS

| | | | |
|---|---|---|---|
| 4,802,487 A * | 2/1989 | Martin et al. | |
| 4,973,305 A * | 11/1990 | Goltzer | |
| 5,084,016 A * | 1/1992 | Freeman et al. | |
| 5,119,832 A * | 6/1992 | Xavier | |
| 5,167,239 A * | 12/1992 | Cohen et al. | |
| 5,215,105 A * | 6/1993 | Kizelshteyn et al. | |
| 5,423,877 A * | 6/1995 | Mackey | |
| 5,505,700 A * | 4/1996 | Leone et al. | |
| 5,626,618 A * | 5/1997 | Ward et al. | |
| 5,690,642 A * | 11/1997 | Osborne et al. | |
| 5,733,322 A * | 3/1998 | Starkebaum | |
| 5,740,808 A * | 4/1998 | Panescu et al. | |
| 5,824,037 A * | 10/1998 | Fogarty et al. | |
| 6,470,209 B2 * | 10/2002 | Snoke | 600/478 |
| 6,510,347 B2 * | 1/2003 | Borkan | |
| 6,554,802 B1 * | 4/2003 | Pearson et al. | |
| 6,607,544 B1 * | 8/2003 | Boucher et al. | |
| 6,999,819 B2 * | 2/2006 | Swoyer et al. | |
| 7,099,718 B1 * | 8/2006 | Thacker et al. | |
| 7,273,468 B2 * | 9/2007 | Bedell | |
| 7,359,755 B2 * | 4/2008 | Jones et al. | |

OTHER PUBLICATIONS

Medtronic, Inc.; Low Complication Catheter Implant Technique; 17 pgs.; Powerpoint. 2003.*

Medtronic, Inc.; Neurostimulators and Their Selection; Jan. 6, 2006; 6 pgs.; www.medtronic.com/neuro/paintherapieslpain_treatment_ladderIneurostimulationsIsti.*

* cited by examiner

METHOD OF IMPLANTING A SPINAL CORD STIMULATOR LEAD HAVING MULTIPLE OBSTRUCTION-CLEARING FEATURES

CROSS-REFERENCE TO RELATED APPLICATIONS

This application is a continuation-in-part of U.S. Non-Provisional patent application Ser. No. 13/270,501, filed Oct. 11, 2011, which is a divisional of U.S. Non-Provisional patent application Ser. No. 11/421,098, filed May 31, 2006, which is a continuation-in-part of U.S. Non-Provisional patent application Ser. No. 11/217,061, filed Aug. 31, 2005, which claims priority to U.S. Provisional Patent Application Ser. No. 60/606,172, filed Aug. 31, 2004, all of which are hereby incorporated herein by reference in their entireties for all purposes.

TECHNICAL FIELD

The present invention relates generally to the field of surgical instruments and methods, and more particularly to a method of implanting a spinal cord stimulator lead into an epidural space having a tissue obstruction.

BACKGROUND

Spinal cord stimulation is used to alleviate chronic pain by stimulating the central nervous system. Conventional spinal cord stimulator leads include percutaneous leads and surgical leads. Percutaneous leads, such as the Medtronic PISCES-Quad® or Octad® leads or the ANS Octrode® and Quattrode® leads, are solid and have a plurality, but typically four or eight, electrode contacts. The percutaneous leads can be inserted through a needle and placed in the epidural space, in close proximity to the spinal cord. When activated, the contacts deliver a precise, mild electrical impulse to the spinal cord or to a peripheral nerve. The electrical impulses activate pain inhibitory mechanisms to block the pain signal from reaching the brain.

However, accurately placing known contacts can be rather difficult because the epidural space that surrounds the spinal cord typically contains fat, veins, adhesions, and connective tissue membranes which interfere with, and often prevent, the accurate placement of the contacts. Using current surgical equipment, a surgeon sometimes inserts a spinal cord stimulator lead and encounters such a tissue obstruction before reaching the emplacement/treatment site, and is then forced to remove it and insert an implement to try clearing the obstruction, if that doesn't work then remove that and insert a different implement to try clearing the obstruction, and then remove that and reinsert the stimulator lead for use to treat the condition. All of this insertion, removal, insertion, removal, insertion, removal, and reinsertion presents increased risks of injuring the spinal cord of the patient.

Therefore, a need exists for an apparatus and method which would allow for greater ease in placing percutaneous contacts in the epidural space, particularly when there are tissue obstructions.

SUMMARY

In one aspect, the present invention relates to a spinal cord stimulator lead for placement in the epidural space of a human or animal subject. The stimulator lead includes a biocompatible body portion defining an elongate shaft, at least a portion of which is flexible; at least one contact positioned along the shaft; two separate lumens extending axially through at least a substantial portion of the shaft with each of the lumens for carrying a fluid; and a distensible balloon positioned around a distal end portion of the shaft and in fluid communication with the second lumen. Preferably, the balloon is a cuffed balloon that expands radially outwardly from at least a portion of the shaft's distal-end portion to compress/clear a tissue obstruction in the epidural space. The second lumen carries a second sterilized fluid under sufficient pressure to expand the balloon. The first lumen is for discharging a first sterilized fluid, such as a pressurized saline solution, corticosteroid, and/or hyaluronidase, directly onto the tissue obstruction to form at least a partial/pilot opening in the tissue obstruction into which the shaft distal-end portion (or at least a portion thereof) can be inserted before expanding the balloon. The spinal cord stimulator lead can have the form of a percutaneous lead or a surgical lead. Additionally, the spinal cord stimulator lead can include a stylet for guiding the stimulator lead into and through the epidural space. Optionally, the spinal cord stimulator lead can include a radiographic marker on the shaft for observation of the stimulator lead under fluoroscopy.

In another aspect, the present invention relates to a method of implanting a spinal cord stimulator lead in the epidural space. The method includes the steps of inserting a spinal cord stimulator lead into the epidural space until blocked by a tissue obstruction, the lead having a shaft, two lumens extending axially through at least a substantial portion of the shaft each for carrying a fluid, the first lumen having an axial outlet at a distal tip of a distal-end portion of the shaft and the second lumen having a radial (or axial) outlet at the distal-end portion of the shaft, and a distensible balloon positioned radially around (or axially beyond) a distal-end portion of the shaft and in fluid communication with the second lumen; discharging the first fluid through the first lumen axial outlet and into the epidural space to at least partially displace a tissue obstruction and thereby form a partial/pilot opening in the tissue obstruction; if the tissue obstruction is not sufficiently displaced then further inserting/advancing the lead in the epidural space at least partially into the partial/pilot opening in the tissue obstruction and inflating and deflating the balloon to further displace the tissue obstruction to form a full/final opening with the tissue obstruction sufficiently displaced to permit passage of the lead therethrough, wherein the balloon expands radially outwardly relative to the shaft's distal-end portion; and guiding the stimulator lead through the full/final opening past the cleared tissue obstruction and into a desired position in the epidural space. The spinal cord stimulator lead has at least one contact, and the method further includes delivery of therapeutic energy to tissue adjacent the contacts.

As such, the first pressurized fluid can be delivered to at least partially displace the tissue obstruction and thereby form a partial/pilot opening in it, the balloon can be advanced into the pilot opening, the second pressurized fluid can be discharged to inflate the balloon to further displace the tissue obstruction and thereby form a full/complete opening in it, and the stimulator lead can be advanced past the cleared obstruction into place then operated to deliver therapeutic electrical impulses, all using only the stimulator lead, all without removing and reinserting the lead relative to the epidural space, and all without inserting and removing any special tissue-obstruction clearing implements relative to the epidural space. Additionally, the method can include the steps of using fluoroscopy to guide placement of the spinal cord stimulator lead and suturing the spinal cord stimulator lead in the desired position in the epidural space.

In yet another aspect, the present invention relates to a kit. The kit includes a needle, a sterile drape, a fluid coupling, a spinal cord stimulator lead having at least one contact, at least two fluid-delivery lumens, a distensible balloon positioned around a distal-end portion of the stimulator lead, and suturing supplies.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the example embodiments are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
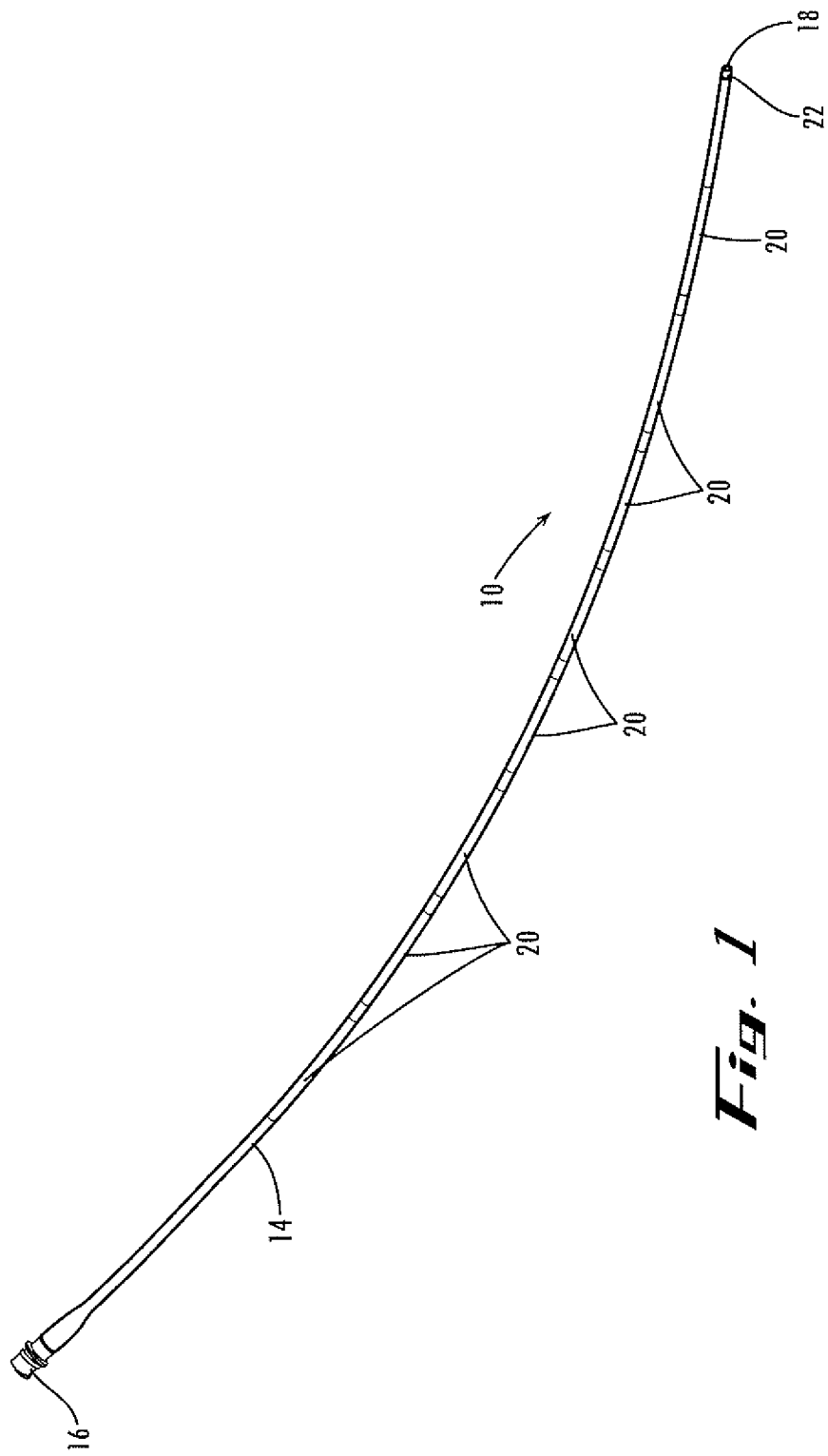
FIG. 1 is a perspective view of a spinal cord stimulator lead according to a first example embodiment of the present invention, showing a discharge outlet of a fluid-delivery lumen extending therethrough for direct injection of pressurized fluid against, and resulting displacement of, a tissue obstruction in an epidural space.
Figure 2:
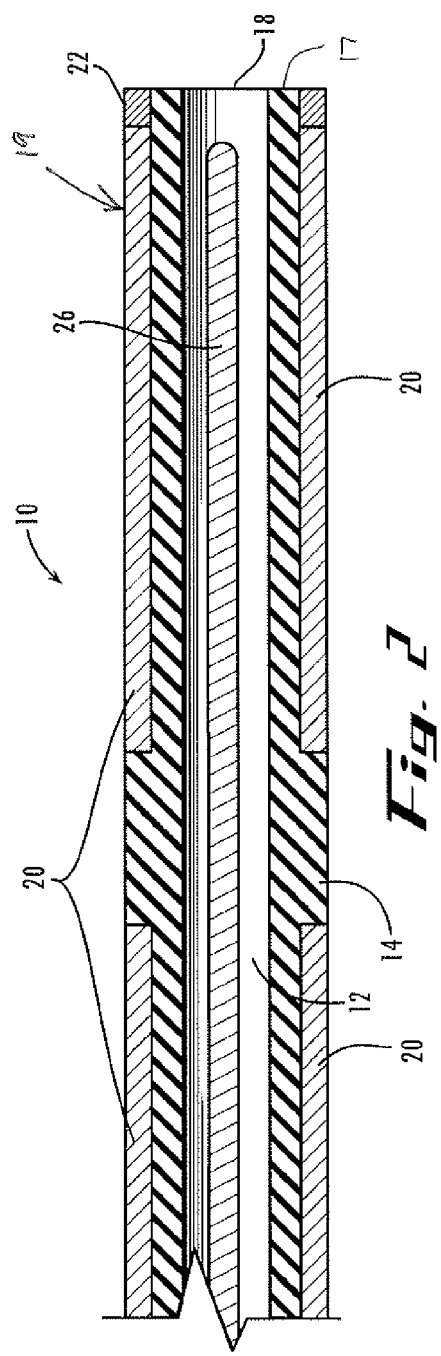
FIG. 2 is a longitudinal cross-sectional view of a distal-end portion of the spinal cord stimulator lead of FIG. 1, showing a portion of the fluid-delivery lumen and its discharge outlet.

Referring to FIGS. 1 and 2, a spinal cord stimulator lead 10 having a fluid-delivery lumen (e.g., a conduit or canal) 12 extending therethrough is described by way of a first example embodiment. The spinal cord stimulator lead 10 can take the form of a percutaneous lead or a surgical paddle lead, for example. Preferably, the spinal cord stimulator lead 10 has a biocompatible, somewhat flexible, electrically non-conductive, cylindrical shaft 14. Exemplary materials that can be used to construct the shaft 14 include, but are not limited to, silicone, polyurethane, or polyethylene. Those skilled in the art will understand that various other biocompatible or biologically inert materials of construction can be used as well, without deviating from the scope of the present invention. The shaft 14 optionally includes a polyurethane insulation sheath for increased durability and longevity. The fluid delivery lumen 12 preferably extends through or along substantially the entire length of the shaft 14 for carrying a fluid, such as a saline solution, from a fluid source (not shown) directly to an area of a tissue obstruction within the subject's epidural space. As used herein, the term tissue obstruction refers to any fat, vein, adhesion, connective tissue, or other obstruction or blockage in the epidural space that interferes with the proper placement (i.e., prevents the advancement and passage) of the spinal cord stimulator lead 10 for use in neurostimulation.

Preferably, the stimulator lead 10 has a connector 16, such as a "leur-lock" type connector, at a proximal end of its shaft 14, for connecting to a fluid source under pressure (not shown) to deliver fluid into the lumen 12. Those skilled in the art will understand that various other connectors for connecting the spinal cord stimulator lead 10 to the fluid source, and that various conventional fluid containers (holding the fluid source) can be employed without deviating from the scope of the present invention. A first discharge outlet 18 of the lumen 12 extends axially through a distal tip (i.e., transverse surface) 17 of a distal-end portion 19 (i.e., opposite the connector 16) of the shaft 14 of the stimulator lead 10 for discharging the fluid from the lumen 12.

The lumen 12 delivers the pressurized fluid for direct injection into the area of the tissue obstruction to at least partially displace the tissue obstruction. For example, a saline solution can be injected into the area of the tissue obstruction to help break up the obstruction. In one example embodiment, a mixture of saline, corticosteroid, and hyaluronidase is injected into the site of the tissue obstruction, via the fluid lumen 12 at its axial outlet 18, to reduce the inflammation. Preferably, the volume of the mixture is not more than about 20 milliliters. Also preferably, the amount of the hyaluronidase is limited to about 150 USP units to no more than about 1500 USP units, while the amount of the corticosteroid administered depends on the type of corticosteroid used. Those skilled in the art will understand how to determine the amount of corticosteroid to administer.

As such, the first fluid commonly includes an anti-inflammatory drug (e.g., corticosteroid or the like) to reduce the size of the tissue obstruction, an accelerant (e.g., hyaluronidase or the like) to increase tissue permeability and thereby speed the dispersion and delivery of the anti-inflammatory drug, and an inert carrier fluid (e.g., saline or the like), with the mixture discharged as a pressurized jet directly onto the tissue obstruction to pressure-ablate at least a partial/pilot (or full/final) opening therein to at least partially displace it. Of course, the first fluid can include only the carrier fluid discharged as a pressurized jet, it can include only the anti-inflammatory drug and the carrier fluid, or it can include an additional drug, as may be desired for a given use.

The spinal cord stimulator lead 10 includes at least one, and preferably, a plurality of electrode contacts 20 for spinal cord stimulation. Preferably, the plurality of contacts 20 comprises four or eight cylindrical contacts spaced along the length of the stimulator lead 10. One or more wires or other electrical conductors are embedded in or on the body 14 to deliver electrical signals from a power source (not shown) to the contacts 20. The first example embodiment of FIGS. 1 and 2, for example, has eight such contacts 20. In a typical such embodiment, each of the eight contacts is about 52 mm long, with the stimulator lead being about 60 cm long. In another embodiment, the stimulator lead 10 includes four contacts 20, each contact being about 24-34 mm long, and the stimulator lead being about 30 cm long. In example embodiments, the spinal cord stimulator lead 10 has a diameter of about 0.8 mm to about 1.5 mm, though those skilled in the art will understand that the size of the diameter larger or smaller. Those skilled in the art will also understand how to configure the stimulator lead and how to determine, for example, contact material, size, shape, span, and spacing. Appropriate selection of the stimulator lead size and contact configuration can be made in accordance with accepted medical protocol as determined by the treating physician.

Optionally, the spinal cord stimulator lead 10 includes a marker 22, such as a radiographic strip or band near the distal tip 17 of the stimulator lead. The marker can aid the practitioner in guiding the stimulator lead 10 under fluoroscopy or other conventional imaging techniques into a proper placement in the epidural space.

Optionally, the stimulator lead 10 can include a stylet 26 positionable within the fluid lumen 12. Preferably, the stylet 26 is a slender and substantially rigid, but malleable, surgical wire for guiding the stimulator lead 10 into and through the soft tissue. The stylet 26 is typically but not necessarily metallic and gives the stimulator lead 10 the resilience to resist minor resistance. Such use of surgical wire allows the practitioner to view the location of the stylet with conventional imaging technology. The stylet 26 can be straight or can be angled (e.g., a small bend at the distal end), such as curved at an angle of about 30° to about 45°, to improve steerablilty and control to assist the physician in steering the lead nonlinearly (e.g., from left to right). In instances where the stylet 26 is angled, preferably, the shape of the stimulator lead 10 conforms to angle of the stylet. Preferably, the stylet 26 is removable from the spinal cord stimulator lead 10 such that once the stimulator lead encounters a tissue obstruction, the stylet can be removed and the lumen 12 can be fitted with a connector, such as a male leur-lock connector 16, and coupled to a fluid source for delivering fluid directly to the area of the obstruction. Alternatively, the stylet 26 can extend through a second or third lumen of the stimulator lead 10 such that the first lumen 12 can be used for fluid injection while simultaneously guiding the stimulator lead with the stylet. In such embodiments, the stylet lumen can be diametrically sized much smaller than the fluid lumen(s). Also optionally, a fiber optic scope could be inserted through the lumen for visualization of internal tissue.

Figure 3:
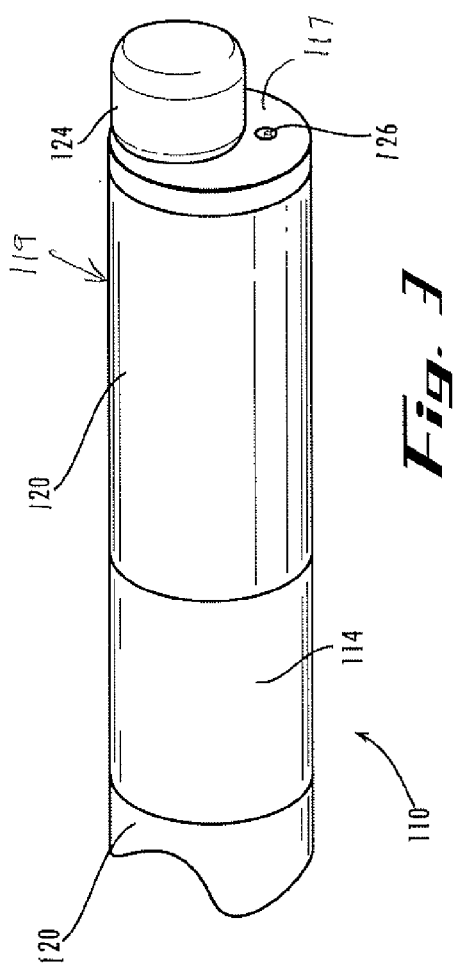
FIG. 3 is a perspective view of a distal-end portion of a spinal cord stimulator lead according to a second example embodiment, showing an expandable balloon mounted thereon, in a contracted position, for cooperating with a second fluid-delivery lumen and thereby displacing tissue obstructions.
Figure 4:
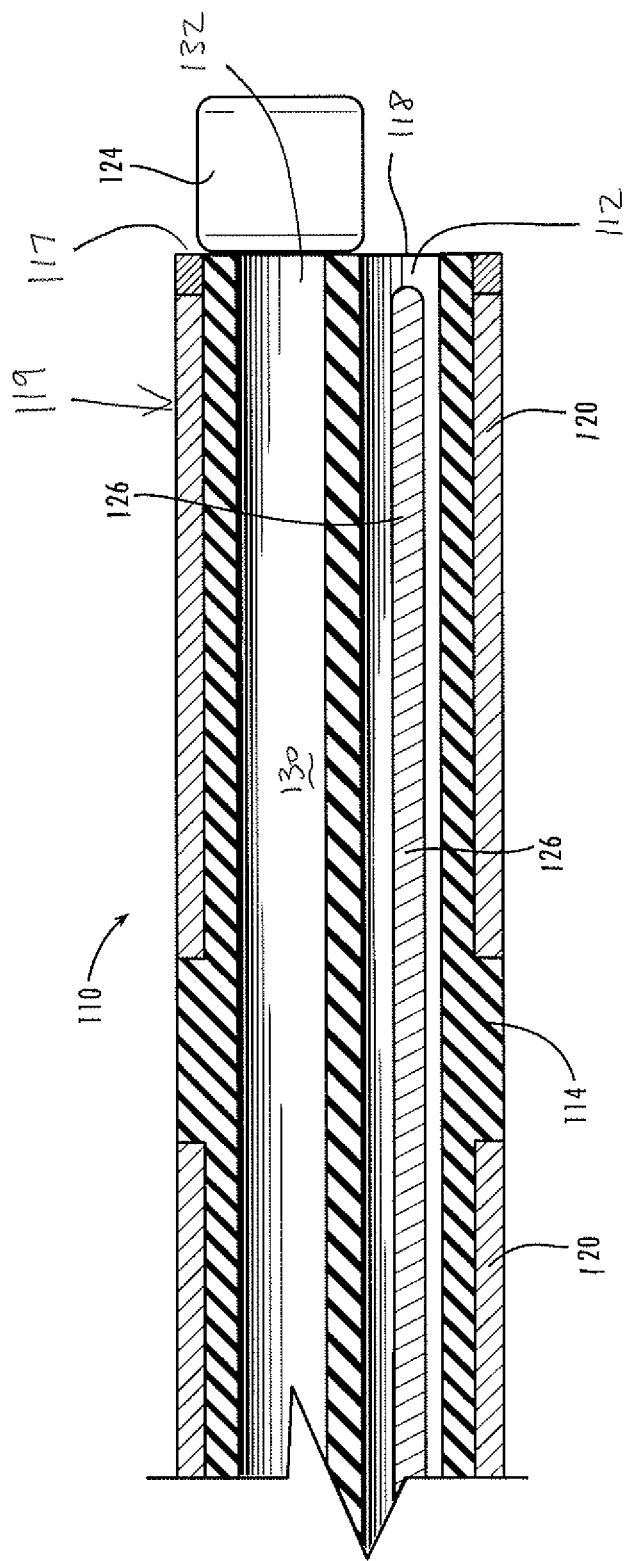
FIG. 4 is a cross-sectional view of a distal-end portion of the spinal cord stimulator lead of FIG. 3, showing portions of the first and second fluid-delivery lumens and their discharge outlets.

A spinal cord stimulator lead 110 according to a second example embodiment of the present invention is shown in FIGS. 3 and 4. The spinal cord stimulator lead 110 comprises a plurality of contacts 120, in substantially similar fashion to the stimulator lead 10 described above, with one or more wires or other electrical conductors embedded in or on the shaft 114 to deliver electrical signals from a power source to the contacts. The spinal cord stimulator lead 110 also includes the first lumen 112 for jetting the first pressurized fluid directly onto the tissue obstruction. As such, the spinal cord stimulator lead 110 is substantially similar to the spinal cord stimulator lead 10 described above, but with the exceptions noted herein.

The stimulator lead 110 of this embodiment further comprises an inflatable and deflatable balloon 124. The balloon 124 is axially positioned and connected to the shaft 114 at the distal-end portion 119 of the spinal cord stimulator lead 10, in fluid communication with a second fluid lumen 130 extending through the shaft via an axial second discharge outlet 132 in a distal tip 117 of the shaft 114. The second lumen 130 delivers fluid, such as a sterilized liquid or air, from a remote fluid source under sufficient pressure to inflate and deflate the balloon 124. The balloon 124 is constructed of a durable, yet distensible, material such as latex, although the present invention also contemplates the use of other distensible, biocompatible materials. The practitioner can alternately inflate and deflate the balloon 124 to displace tissue obstructions that prevent the passage and placement of the spinal cord stimulator lead 110. Thus, discharging the first fluid into the balloon 124 in a deflated state will expand the balloon radially outward to an inflated state and thereby impart a radial-compressive force on the tissue obstruction to compress it radially outward to further displace it thereby expanding the pilot opening into a full opening. Optionally, the balloon 124 is detachable and retractable through the lumen 130, so that once the spinal cord stimulator lead 110 is properly placed, the practitioner can disengage the balloon 124 from the stimulator lead and remove it, with, for example, the stylet 126 or some other device.

In this embodiment, the first lumen 112 is used to deliver fluid directly to the area of the tissue obstruction via the axial discharge outlet 118 to at least partially clear the tissue obstruction, while the second lumen 130 is used if needed to deliver fluid to distend the balloon 124 to further clear the tissue obstruction. Preferably, the stylet 126 is positionable with the first lumen 112 to guide and steer the stimulator lead 110 through the soft tissue and into the epidural space (as depicted). Alternatively, the stylet 126 can be positionable within a third lumen extending axially through the shaft to guide and steer the stimulator lead 110 through the soft tissue and into the epidural space.

Figure 5:
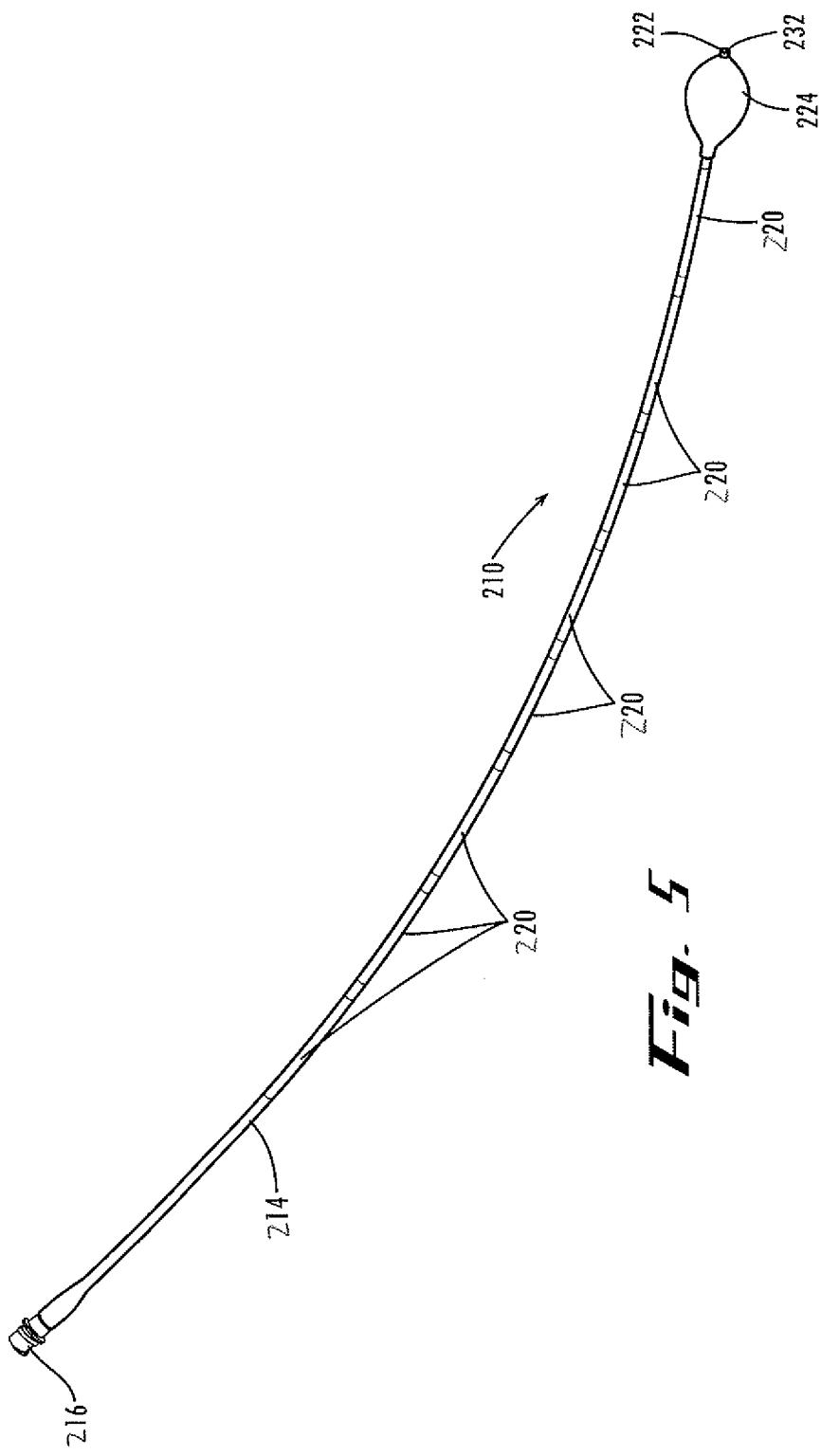
FIG. 5 is a perspective view of a spinal cord stimulator lead according to a third example embodiment of the present invention, showing an expandable balloon mounted thereon, in an expanded position, for cooperating with a second fluid-delivery lumen and thereby displacing tissue obstructions.
Figure 6:
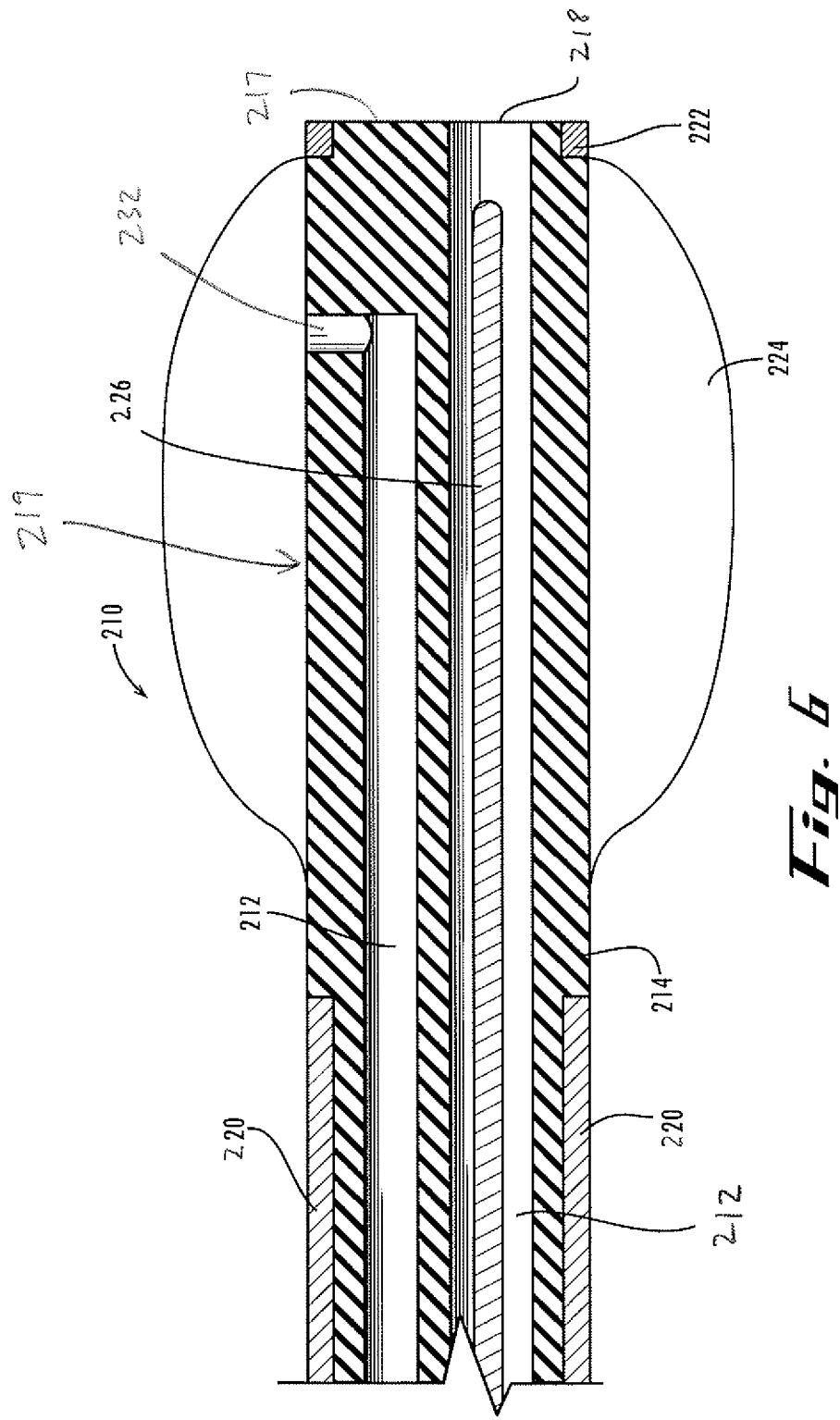
FIG. 6 is a cross-sectional view of a distal-end portion of the spinal cord stimulator lead of FIG. 5, showing portions of the first and second fluid-delivery lumens and their discharge outlets.

A third example embodiment of the spinal cord stimulator lead 210 is shown in FIGS. 5 and 6. The spinal cord stimulator lead 210 comprises a plurality of contacts 220, in substantially similar fashion to the stimulator lead 110 described above with one or more wires or other electrical conductors embedded in or on the shaft 214 to deliver electrical signals from a power source to the contacts. The spinal cord stimulator lead 210 is substantially similar to the spinal cord stimulator lead 110, but with the exceptions noted herein.

The spinal cord stimulator lead 210 of this embodiment includes a cuffed balloon 224 located around a distal-end portion 219 thereof. Preferably, the cuffed balloon 224 has a generally oblong shape in the sense that the balloon is longer (axially) than it is wide (radially) when the balloon is inflated. In an example embodiment, the balloon 224 extends from the distal-end portion 219 near the distal tip 217 of the shaft 214. For example, in the depicted embodiment the balloon 224 extends from the distal-end portion 219 of the shaft 214 with only a retaining collar 222 between the balloon and the distal tip 217. The cuffed balloon 224 is in fluid communication with the second lumen 230 such that the balloon can expand generally radially outwardly about all or a portion of the circumference of the shaft 214 at the distal-end portion 219 of the spinal cord stimulator lead 110. Preferably, the balloon 224 can be expanded to a size of about four to six times greater than the diameter of the shaft 214 of the stimulator lead 110. Thus, preferably, the length of the balloon 224 is at least, and more preferably, greater than four to six times greater than the diameter of the shaft 214. The stimulator lead 210 also includes a first lumen 212 extending therethrough for discharging fluid directly into an area of a tissue obstruction via an axial discharge outlet 218 in a distal tip 217 of the shaft 214.

The second lumen 230 carries a second fluid, such as a sterilized liquid or air, under sufficient pressure to inflate and deflate the balloon 224. The diameter of the second lumen 230 for delivering the second fluid to inflate the balloon 224 is preferably smaller than the diameter of the first lumen 212 for carrying a fluid directly to the site of the tissue obstruction. However, those skilled in the art will understand that the first and second lumens 212 and 230 can have substantially the same diameter, or the diameter of the first lumen for delivering fluid directly to the site of the obstruction can be smaller than the second lumen for carrying fluid to the balloon 224.

Those skilled in the art will also understand that one or both of the first and second fluid lumens 212 and 230 can extend along the outer body of the shaft 214 or within the shaft 214, and the first lumen 212 can also serve as the lumen for receiving the stylet 26. Alternatively, a third lumen can be provided in the shaft 214 to serve as the lumen for the stylet 26.

Preferably, the balloon 224 is constructed of a durable, yet distensible, material such as latex, although the present invention also contemplates the use of other distensible, biocompatible materials. The practitioner can alternately inflate and deflate the balloon 224 to laterally displace tissues of the tissue obstruction preventing the passage or placement of the spinal cord stimulator lead 210.

Figure 7:
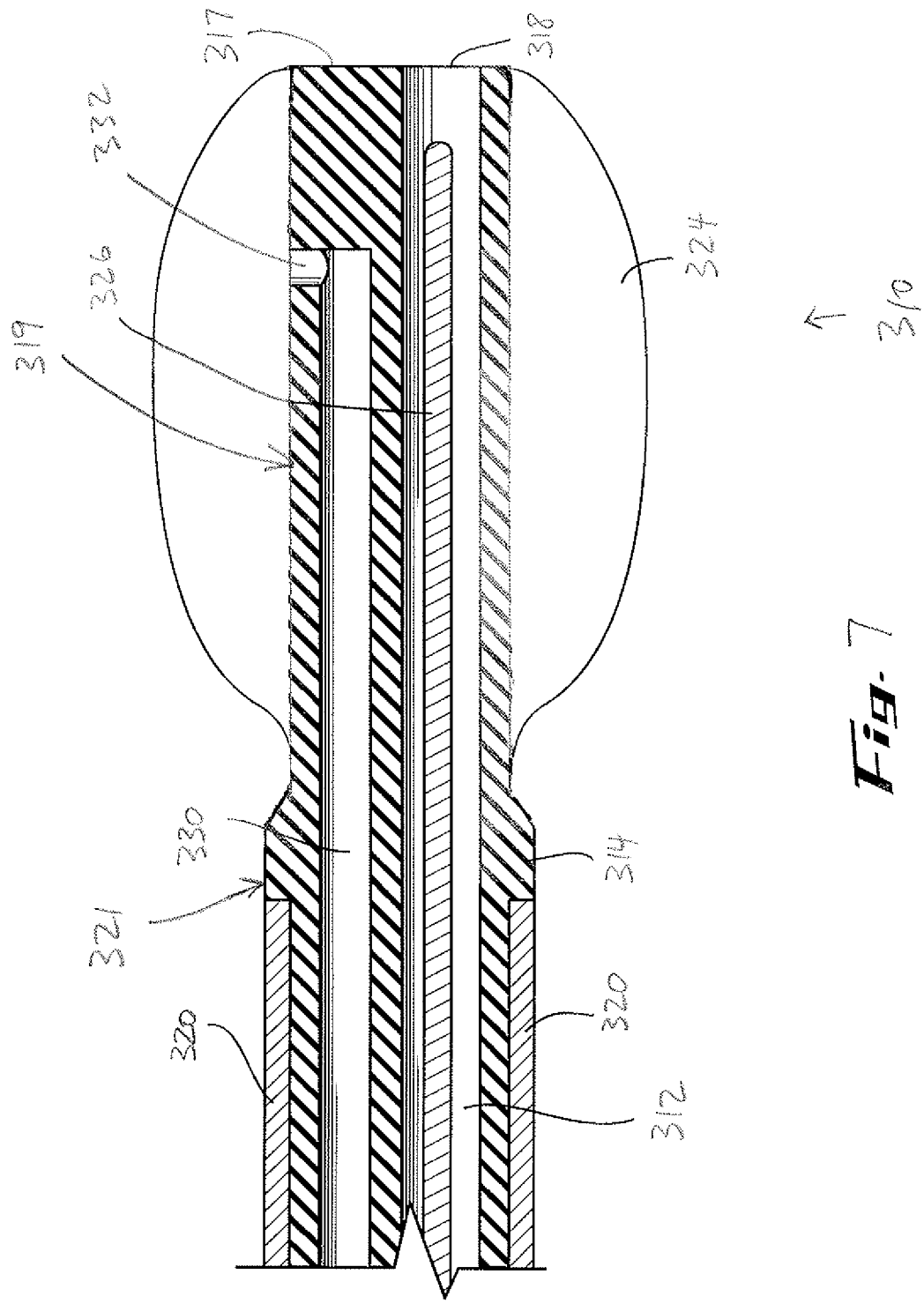
FIG. 7 is a cross-sectional view of a distal-end portion of a spinal cord stimulator lead according to a fourth example embodiment of the present invention.

FIG. 7 shows a portion of a spinal cord stimulator lead 310 according to a fourth example embodiment. This embodiment is substantially similar to the spinal cord stimulator leads 110 and 210 described above. For example, the stimulator lead 310 includes a shaft 314 defining first and second lumens 312 and 330, a contact portion 321, a distal-end portion 319, and a distal tip 317, with the first lumen having an axial discharge outlet 318 and the second lumen having a radial discharge outlet 332. Also substantially similarly, the stimulator lead 310 includes a distensible balloon 324 at the distal-end portion 319 of the shaft 314, and a plurality of contacts 320 positioned along the contact portion 321 of the shaft. The first and second lumens 312 and 330 carry first and second fluids the same as described above.

In this embodiment, however, the distal-end portion 319 of the shaft 314 has a smaller diameter than the contact portion 321 of the shaft and as such defines a leading insertion section of the shaft. There are no contacts 320 on the distal-end portion 319 of the shaft 314, and thus no electrical conductors (e.g., wires), so the distal-end portion of the shaft has a diameter that is smaller for example by at least the diametrical thickness of the contacts and the conductors. This enables the distal-end portion 319 (and the distensible balloon 324 mounted onto it) to fit into small-diameter partial/pilot openings pressure-ablated in the tissue obstructions by the first pressurized fluid (or naturally occurring without the need for the first-fluid pressure-ablation). Typically the shaft 314 includes a transition portion that is tapered (e.g., smoothly radially increasing in the proximal direction, as depicted) between the smaller-diameter distal-end portion 319 and the larger-diameter contact portion 320 of the shaft 314.

Figure 8:
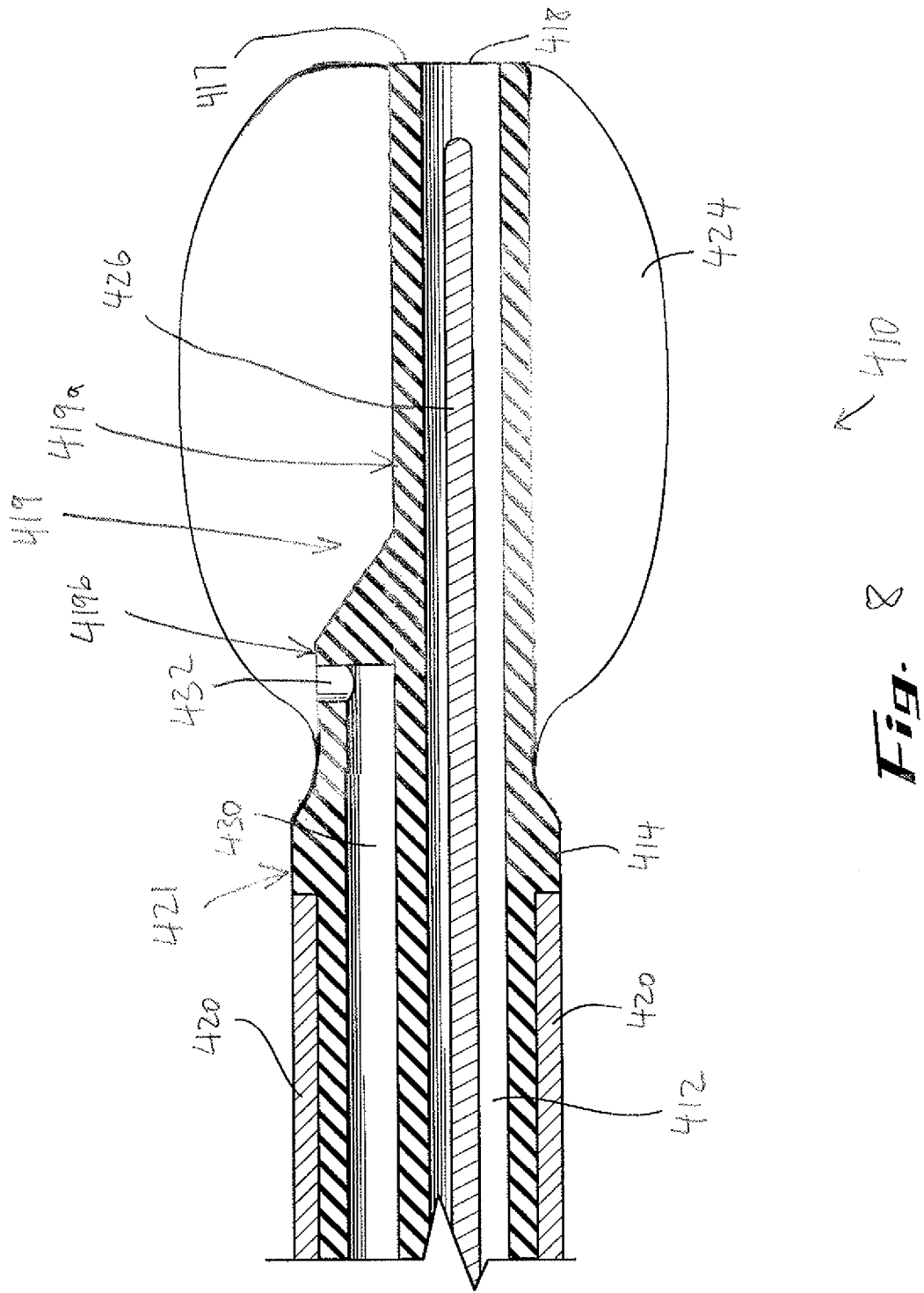
FIG. 8 is a cross-sectional view of a distal-end portion of a spinal cord stimulator lead according to a fifth example embodiment of the present invention.

FIG. 8 shows a portion of a spinal cord stimulator lead 410 according to a fifth example embodiment. This embodiment is substantially similar to the spinal cord stimulator leads 110, 210, and 310 described above. For example, the stimulator lead 410 includes a shaft 414 defining first and second lumens 412 and 430, a contact portion 421, a distal-end portion 419, and a distal tip 417, with the first lumen having an axial discharge outlet 418 and the second lumen having a radial discharge outlet 432. Also substantially similarly, the stimulator lead 410 includes a distensible balloon 424 at the distal-end portion 419 of the shaft 414, and a plurality of contacts 420 positioned along the contact portion 421 of the shaft. The first and second lumens 412 and 430 carry first and second fluids the same as described above.

In this embodiment, however, the distal-end portion 419 of the shaft 414 has an insertion section 419a and an inflation section 419b, both having a smaller diameter than the contact portion 421 of the shaft. The insertion section 419a is for inserting into the pilot opening and is substantially surrounded by the balloon 424, and the inflation section 419b is where the discharge outlet 432 is positioned. There are no contacts 420 on the inflation section 419b of the distal-end portion 419 of the shaft 414, and thus no electrical conductors (e.g., wires), so the inflation section of the distal-end portion of the shaft has a diameter that is smaller for example by at least the diametrical thickness of the contacts and the conductors. And the second lumen 430 terminates in the inflation section 419b of the distal-end portion 419 of the shaft 414 (radially as depicted, or axially in other embodiments), so the insertion section 419a of the distal-end portion of the shaft has a diameter that is smaller for example by at least the diametrical thickness of the second lumen and the shaft wall forming it. This enables the insertion section 419*a* of the distal-end portion 419 (and the distensible balloon 424 mounted onto it) to fit into small-diameter partial/pilot openings pressure-ablated in the tissue obstructions by the first pressurized fluid (or naturally occurring without the need for the first-fluid pressure-ablation). Typically the shaft 414 includes a transition portion that is tapered (e.g., radially increasing in a stepped fashion in the proximal direction, as depicted) between the smaller-diameter distal-end portion 419 and the larger-diameter contact portion 420 of the shaft 414.

By including the first and second lumens 412 and 430 in the shaft 414 of the spinal cord stimulator lead 410 to facilitate displacing tissue obstructions, the diameter of the shaft is not necessarily increased. Conventional stimulator leads have a diameter large enough to carry contacts and control wires, and that diameter is typically large enough that they do not need to be any larger to also include one or two lumens formed inside them. But with the stimulator lead shaft sized large enough to carry contacts and control wires, it can be hard to advance past tissue obstructions. The stimulator lead 410 is designed to provide an insertion section 419*a* of the shaft 414 with a minimized diameter so that it can insert into small-diameter partial/pilot openings in the tissue obstructions that the contact portion 421 cannot fit past, so the obstruction can be radially-outwardly compressed sufficiently to advance the contact portion past it. This same design concept is implemented, only to a somewhat lesser extent, in the stimulator lead 310 of the previous embodiment.

It should be noted that in some embodiments the stimulator lead is provided with a shaft including only one fluid-delivery lumen and a smaller-diameter distal-end insertion portion. The smaller-diameter distal-end insertion portion fits into a smaller partial-pilot opening in an obstruction, and the lumen carries a pressurized fluid to inflate and deflate a balloon to provide for radially-outward compression/expansion of the obstruction to form a larger final opening. In other embodiments, the lumen carries a pressurized fluid to pressure-ablate a smaller partial-pilot opening in an obstruction, and the smaller-diameter distal-end insertion portion fits into the partial-pilot opening in the obstruction and can be advanced so that the radially-outward taper of the shaft transition portion radially-outward compresses/expands the obstruction to form a larger final opening through which the contact portion of the lead shaft can pass.

It should be further noted that in some embodiments the two lumens are generally cylindrical and parallel, with the shaft typically having an oval or elliptical cross-sectional shape, instead of a conventional circular cross-sectional shape. As such, the term "diameter" as used herein is intended to mean the largest lateral (cross-sectional) dimension, which is not necessarily a true "diameter." In other embodiments, the two lumens have a generally semi-circular cross-sectional shape, with the shaft typically having a conventional circular cross-sectional shape. In some other embodiments, the two lumens have a generally semi-circular cross-sectional shape through the contact portion, which thus can have a circular cross-sectional shape, a generally circular cross-sectional shape through the insertion portion of the distal-end portion, which thus can have a circular cross-sectional shape, and transition between the semi-circular and circular cross-sectional shapes in the inflation portion of the distal-end portion, which thus can have a circular cross-sectional shape. In yet other embodiments, the two lumens are coaxial and circular, with the first lumen positioned inside the annular second lumen, and with the shaft typically being circular along its entire length. And in still yet other embodiments, the shaft includes a single lumen with the first and second discharge outlets and a remote-controlled valve in the lumen for selectively directing a single sterilized fluid through one or the other of the outlets.

And it should be still further noted that in typical embodiments the proximal-end portion of the stimulator lead shaft has the same diameter and shape as the distal-end portion. This is because in typical use the proximal-end portion will eventually fit/snap into a battery or connecting cable. As such, in some embodiments such as those depicted in FIGS. 7-8, the contact portion of the lead shaft has a larger diameter than the proximal-end portion and the distal-end portion.

An example method of use will now be described with reference to the spinal cord stimulator lead 410 of the fifth embodiment and FIGS. 9-16, though it is applicable to the spinal cord stimulator leads of the second through fourth embodiments too. First, a guide needle (not shown) is positioned generally in the epidural space 6 of a human or animal subject. The spinal cord stimulator lead 410 along with the stylet 426 are inserted through the guide needle into the epidural space 6. Preferably, the practitioner uses fluoroscopy (not shown) to guide the placement of the guide needle and/or the stimulator lead 410.

Figure 11:
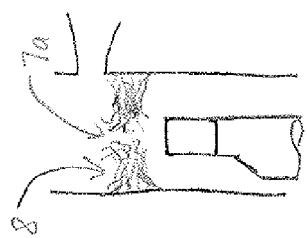
FIG. 11 shows the stimulator lead and epidural space portions of FIG. 10 with the pilot opening formed in the tissue obstruction.
Figure 16:
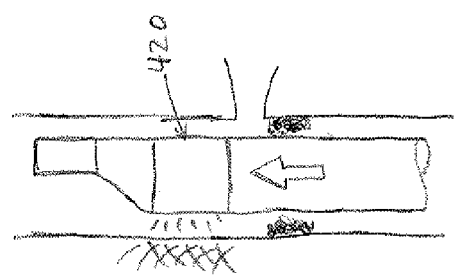
FIG. 16 shows the stimulator lead and epidural space portions of FIG. 15 with the stimulator lead advanced past the cleared tissue obstruction and an contact actuated to deliver therapeutic energy to a treatment suite.
Figure 10:
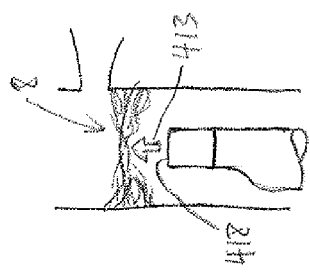
FIG. 10 shows the stimulator lead and epidural space portions of FIG. 9 with the first fluid being discharged through the first lumen to pressure-ablate a pilot opening in the tissue obstruction.
Figure 9:
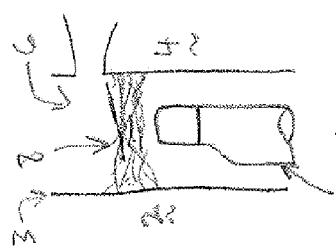
FIG. 9 is a side schematic view of the stimulator lead portion of FIG. 8 in use according to an example method of the invention, showing the stimulator lead inserted into a portion of an epidural space and encountering a tissue obstruction.

As the practitioner is guiding the stimulator lead 410 into the desired location in the epidural space 6, between the dura 3 (surrounding the spinal cord 2) and the spinous process 4, sometimes a tissue obstruction 8 is encountered that blocks (at least interferes with) further advancement of the stimulator lead to accurately place the contacts (FIG. 9). To clear the tissue obstruction 8 for advancement of the stimulator lead 410, the practitioner can remove the stylet 426 and connect the stimulator lead to a first fluid source (not shown). Then the practitioner can inject the first fluid 413 from the first fluid source through the first lumen 412 axially into the epidural space directly onto the tissue obstruction 8 to at least partially displace the tissue obstruction 8 (FIG. 10). For example, the practitioner can operate controls (e.g., valving) of the first fluid source to control pressurized flow of the first fluid 413 through the first lumen and out of the first outlet 418 with sufficient pressure to pressure-ablate the tissue obstruction 8 until a pilot opening 7*a* is formed (FIGS. 10-11). This is continued until the pilot opening 7*a* in the tissue obstruction 8 is formed with a general (not necessarily uniform) diameter that is about as large or larger than a diameter (or other largest lateral dimension) of the insertion section 419*a* of the distal-end portion of the stimulator lead 410.

Figure 12:
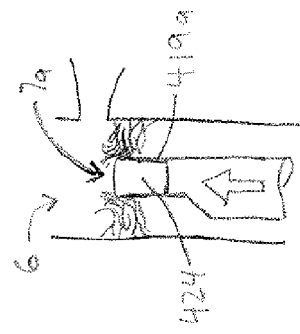
FIG. 12 shows the stimulator lead and epidural space portions of FIG. 11 with the stimulator lead being advanced to position the balloon in the pilot opening in the tissue obstruction.
Figure 15:
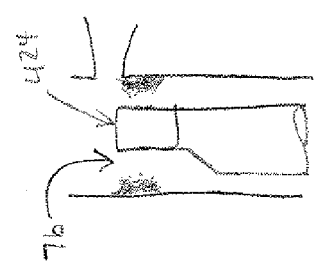
FIG. 15 shows the stimulator lead and epidural space portions of FIG. 13 with the balloon deflated back to its neutral position.
Figure 13:
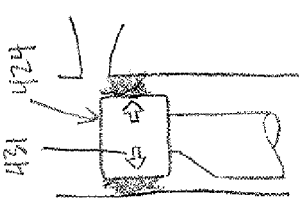
FIG. 13 shows the stimulator lead and epidural space portions of FIG. 14 with the second fluid being discharged through the second lumen to inflate the balloon to expand the pilot opening to form a final opening in the tissue obstruction.
Figure 14:
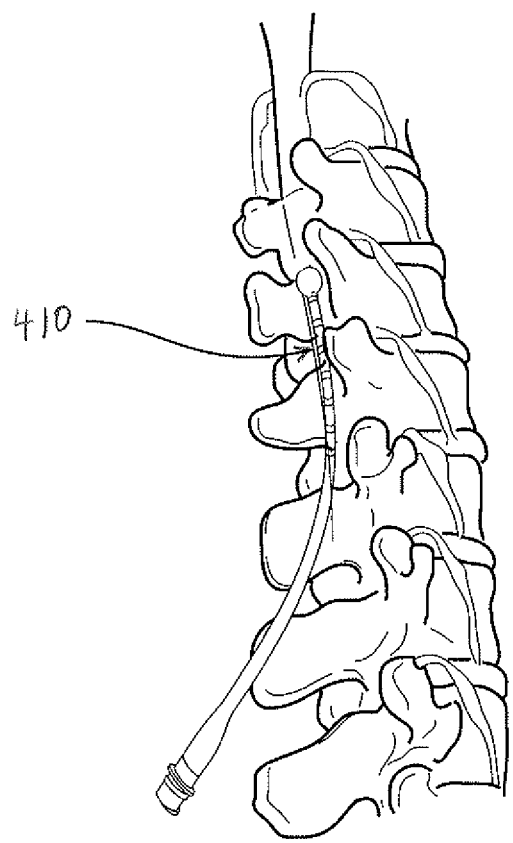
FIG. 14 is a perspective view of the spinal cord stimulator lead and epidural space of FIG. 13.

Next, the practitioner advances the stimulator lead 410 (as indicated by the directional arrow) further into epidural space 6 until the insertion section 419*a* of the distal-end portion 419 of the stimulator lead 410, or at least the balloon 424 mounted to it (or extending axially from it, as in the second embodiment), are positioned within the pilot opening 7*a* (FIG. 12). Then, the practitioner directs delivery of the second fluid 431 from the second fluid source through the second lumen 430 to expand and contract the balloon 424 for further displacement of the tissue obstruction 8. For example, the practitioner can operate controls (e.g., valving) of the second fluid source (not shown) to control pressurized flow of the second fluid 431 through the second lumen and out of the second outlet with sufficient pressure to inflate the balloon radially outward relative to the distal-end portion of the stimulator-lead shaft until the pilot opening is expanded (FIGS. 13-14). Once the pilot opening has been expanded to form the final opening 7*b*, the balloon 424 is deflated back to its neutral position, for example by disconnecting the second fluid source and permitting the second pressurized fluid to flow out through the second lumen (FIG. 15). The final opening 7b in the tissue obstruction 8 is formed with a general (not necessarily uniform) diameter that is about as large or larger than a diameter (or other largest lateral dimension) of a largest-diameter portion of the stimulator lead 410 to permit the stimulator lead to be advanced past the cleared tissue obstruction and into place.

The stimulator lead 410 is then advanced axially forward (as indicated by the directional arrow of FIG. 16) past the cleared tissue obstruction, positioned as desired in the epidural space of the patient, and typically secured in place with sutures (not shown). The stimulator lead 210 is then disconnected from the first and second fluid sources and connected to a power source (not shown) for delivery of electrical energy to the contacts 420. The power source may be external, or may be implanted internally, for example in the patient's abdomen or elsewhere. An internal or external controller is used to control the power source and activate the contacts 420 to deliver therapeutic energy to a treatment suite (FIG. 16) according to a physician prescribed treatment regimen. The spinal cord stimulator lead 410 thus functions both as a typical catheter when implanting the stimulator lead and as a spinal cord stimulator lead once implanted.

Typically, the pilot opening 7a is formed extending axially all the way through the tissue obstruction 8, as depicted. Alternatively, the pilot opening can be formed extending axially only part of the way through the tissue obstruction (i.e., forming an indentation), the balloon can be inserted thereinto and expanded, the pilot opening can be formed extending axially farther through the tissue obstruction, and the process can be repeated until the full/final opening is formed in the tissue obstruction. As such, the obstruction-clearing process can be further staged in a repeating cycle until the epidural space is sufficiently cleared of the tissue obstruction to permit proper placement of the stimulator lead.

And sometimes the tissue obstruction does not completely block the epidural space, but only partially does so. That is, sometimes it forms a narrowed opening that the balloon can still fit into. In such situations, the first step of pressure-ablating the tissue obstruction to form the pilot opening is not required, and only the second-step of balloon compressing the tissue is needed.

As such, the described method of implanting a stimulator lead includes a serial obstruction-clearing process that does not require the stimulator lead to be removed or any additional obstruction-clearing implements to be removed/inserted relative to the epidural space. In particular, the first pressurized fluid can be delivered to at least partially displace the tissue obstruction and thereby form a partial/pilot opening in it the balloon can be advanced into the pilot opening, the second pressurized fluid can be discharged to inflate the balloon to further displace the tissue obstruction and thereby form a full/complete opening in it, and the stimulator lead can be advanced past the cleared obstruction into place then operated to deliver therapeutic electrical impulses, all using only the stimulator lead, all without removing and reinserting the lead relative to the epidural space, and all without inserting and removing any special tissue-obstruction clearing implements relative to the epidural space. In other words, this three-way method of using a single spinal cord stimulator lead includes delivering the first pressurized fluid to displace at least partially the tissue obstruction by direct flow and axial pressure-ablation, discharge the second pressurized fluid displace the tissue obstruction by radial compression by the inflated balloon, and operating the stimulator lead to deliver therapeutic electrical impulses, without removing and reinserting the stimulator lead from and into to the epidural space. This is a significant advance because it eliminates the need to removal the stimulator lead, insert an implement to try clearing the obstruction, if that doesn't work then remove that and insert a different implement to try clearing the obstruction, and then remove that and reinsert the stimulator lead for use to treat the condition, because all of that insertion, removal, insertion, removal, insertion, removal, and reinsertion presents increased risks of injuring the spinal cord of the patient.

Optionally, the tools and supplies that the practitioner uses to implant the stimulator lead of the present invention into the patient are assembled into a self-contained kit. For example, the kit includes a guide needle, a dual-lumen spinal cord stimulator lead of a type described herein, a sterile drape, a power source, a fluid coupling, and suturing supplies, or any subcombination thereof, within a case or other container.

While the invention has been described with reference to preferred and example embodiments, it will be understood by those skilled in the art that a variety of modifications, additions and deletions are within the scope of the invention, as defined by the following claims.

What is claimed is:
1. A method of implanting a spinal cord stimulator lead into an epidural space of a human or animal subject for treatment, the epidural space having a tissue obstruction, the method comprising:
 providing the spinal cord stimulator lead with:
  a shaft including a longitudinal axis, a distal-end portion having a distal tip that is transverse to the shaft axis, and at least one portion that is flexible;
  at least one contact positioned on the shaft and adapted to deliver an electrical impulse within the epidural space;
  a first lumen extending through at least a portion of the shaft and including a first discharge outlet in the distal tip of the shaft, wherein the first lumen carries a first pressurized fluid and the first outlet discharges the first pressurized fluid directly onto the tissue obstruction to pressure-ablate at least a pilot opening therein;
  a second lumen extending through at least a portion of the shaft and including a second discharge outlet in the distal-end portion of the shaft, wherein the second lumen carries a second pressurized fluid and the second outlet discharges the second pressurized fluid; and
  a distensible balloon positioned at the distal-end portion of the shaft and in fluid communication with the second lumen and the second outlet, wherein the balloon is inflatable by the second pressurized fluid;
 guiding the spinal cord stimulator lead forward in the epidural space until the distal tip of the shaft is adjacent and blocked from further advancement by the tissue obstruction;
 discharging the first pressurized fluid through the first lumen and the first outlet of the shaft directly onto the tissue obstruction thereby imparting a pressure-ablation force on the tissue obstruction to at least partially displace the tissue obstruction and form a pilot opening;
 guiding the stimulator lead further forward until the balloon is positioned within the pilot opening of the partially-displaced tissue obstruction;
 discharging the second pressurized fluid through the second lumen and the second outlet of the shaft and into the distensible balloon to inflate the balloon from a deflated position to an inflated position thereby imparting a radial-compression force on the tissue obstruction to further displace the tissue obstruction and form a final opening;

guiding the stimulator lead further forward through the final opening past the further-displaced tissue obstruction and into a treatment position within the epidural space with the contact adjacent a treatment area; and operating the stimulator lead to deliver therapeutic electrical impulses from the contact to the a treatment area adjacent the contact within the epidural space, wherein the serial steps of delivering the first pressurized fluid to at least partially displace the tissue obstruction, discharging the second pressurized fluid to further displace the tissue obstruction, and operating the stimulator lead to deliver therapeutic electrical impulses are all performed using the stimulator lead in the epidural space, and are all performed without removing and reinserting the stimulator lead relative to the epidural space.

2. The method of claim 1, further comprising exhausting the second pressurized fluid from the distensible balloon in the inflated position, through the second lumen of the shaft, to deflate the balloon to the deflated position.

3. The method of claim 1, wherein the steps of guiding the stimulator lead further comprises guiding a stylet through the first lumen to guide emplacement of the stimulator lead within the epidural space.

4. The method of claim 1, wherein the steps of guiding the stimulator lead further comprise using fluoroscopy to guide emplacement of the stimulator lead within the epidural space.

5. The method of claim 1, further comprising suturing the stimulator lead in the treatment position within the epidural space.

6. The method of claim 1, wherein the first pressurized fluid includes a saline solution, corticosteroid, and hyaluronidase.

7. The method of claim 1, wherein the second pressurized fluid comprises a sterilized fluid under sufficient pressure to expand the balloon to the inflated position.

8. The method of claim 1, further comprising, after the stimulator lead is emplaced in the treatment position, delivering a fluid medication through the first lumen and the first outlet of the shaft directly into the epidural space.

9. The method of claim 1, wherein the spinal cord stimulator lead is a percutaneous lead or a surgical lead.

10. The method of claim 1, wherein the second lumen for inflating the balloon against the tissue obstruction has a smaller diameter than the first lumen for discharging the first pressurized fluid directly onto the tissue obstruction.

11. The method of claim 1, wherein the first outlet is axially formed through the distal tip of the shaft.

12. The method of claim 1, wherein the second outlet is radially formed through the distal end portion of the shaft.

13. The method of claim 1, wherein the step of discharging the second pressurized fluid includes simultaneously manipulating a stylet through the first lumen to attempt advancement of the stimulator lead within the epidural space past the partially-displaced tissue obstruction.

14. The method of claim 1, wherein the shaft includes a contact portion where the contact is mounted, and the distal-end portion of the shaft has a smaller diameter than the contact portion, wherein the step of guiding the stimulator lead further forward until the balloon is positioned within the pilot opening includes advancing at least a portion of the distal-end portion and the balloon into the pilot opening but not the contact portion of the shaft.

15. The method of claim 14, wherein the distal-end portion of the shaft includes an insertion section and an inflation section, wherein the balloon substantially surrounds the insertion section and the second discharge outlet is formed in the inflation section, wherein the inflation section has a smaller diameter than the contact portion, which in turn has a smaller diameter than the insertion section, and wherein the step of guiding the stimulator lead further forward until the balloon is positioned within the pilot opening includes advancing the insertion section and the balloon into the pilot opening but not the inflation section or the contact portion of the shaft.

16. The method of claim 1, wherein the step of discharging the first pressurized fluid includes forming the pilot opening with a larger diameter than the distal-end portion of the shaft.

17. The method of claim 1, wherein the step of discharging the second pressurized fluid includes forming the final opening with a larger diameter than a contact portion of the shaft where the contact is mounted.

18. A method of implanting a spinal cord stimulator lead into an epidural space of a human or animal subject for treatment, the epidural space having a tissue obstruction, the method comprising:

providing the spinal cord stimulator lead with:
  a shaft including a longitudinal axis, a distal-end portion having a distal tip that is transverse to the shaft axis, at least one portion that is flexible, and a contact portion, wherein the distal-end portion of the shaft has a smaller diameter than the contact portion of the shaft;
  at least one contact positioned on the contact portion of the shaft and adapted to deliver an electrical impulse within the epidural space;
  a first lumen extending through at least a portion of the shaft and including a first discharge outlet axially formed in the distal tip of the shaft, wherein the first lumen carries a first pressurized fluid and the first outlet discharges the first pressurized fluid directly onto the tissue obstruction to pressure-ablate at least a pilot opening therein;
  a second lumen extending through at least a portion of the shaft and including a second discharge outlet radially formed in the distal-end portion of the shaft, wherein the second lumen carries a second pressurized fluid and the second outlet discharges the second pressurized fluid, wherein the first and second lumens are separate lumens; and
  a distensible balloon positioned at the distal-end portion of the shaft and in fluid communication with the second lumen and the second outlet, wherein the balloon is inflatable by the second pressurized fluid;

guiding the spinal cord stimulator lead forward in the epidural space until the distal tip of the shaft is adjacent and blocked from further advancement by the tissue obstruction;

discharging the first pressurized fluid through the first lumen and the first outlet of the shaft directly onto the tissue obstruction thereby imparting an axial pressure-ablation force on the tissue obstruction to at least partially displace the tissue obstruction and form a pilot opening with a larger diameter than the distal-end portion of the shaft;

guiding the stimulator lead further forward until at least a portion of the distal-end portion and the balloon are positioned within the pilot opening of the partially-displaced tissue obstruction but the contact portion of the shaft is not;

discharging the second pressurized fluid through the second lumen and the second outlet of the shaft and into the distensible balloon to inflate the balloon from a deflated position to an inflated position thereby imparting a radial-compression force on the tissue obstruction to further displace the tissue obstruction and form a final opening with a larger diameter than the contact portion of the shaft;

exhausting the second pressurized fluid from the distensible balloon in the inflated position, through the second lumen of the shaft, to deflate the balloon to the deflated position;

guiding the stimulator lead further forward through the final opening past the further-displaced tissue obstruction and into a treatment position within the epidural space with the contact adjacent a treatment area; and operating the stimulator lead to deliver therapeutic electrical impulses from the contact to the a treatment area adjacent the contact within the epidural space, wherein the serial steps of delivering the first pressurized fluid to at least partially displace the tissue obstruction, discharging the second pressurized fluid to further displace the tissue obstruction, and operating the stimulator lead to deliver therapeutic electrical impulses are all performed using the stimulator lead in the epidural space, and are all performed without removing and reinserting the stimulator lead relative to the epidural space.

19. The method of claim 18, wherein the step of discharging the second pressurized fluid includes simultaneously manipulating a stylet through the first lumen to attempt advancement of the stimulator lead within the epidural space past the partially-displaced tissue obstruction.

20. The method of claim 18, wherein the distal-end portion of the shaft includes an insertion section and an inflation section, wherein the balloon substantially surrounds the insertion section and the second discharge outlet is formed in the inflation section, wherein the inflation section has a smaller diameter than the contact portion, which in turn has a smaller diameter than the insertion section, and wherein the step of guiding the stimulator lead further forward until the balloon is positioned within the pilot opening includes advancing the insertion section and the balloon into the pilot opening but not the inflation section or the contact portion of the shaft.

* * * * *